(12) United States Patent
Kamimura et al.

(10) Patent No.: US 7,192,754 B2
(45) Date of Patent: Mar. 20, 2007

(54) *NOMURAEAE RILEYI*-ORIGIN ECDYSTEROID 22-OXIDASE AND MOLT HORMONE INACTIVATION SYSTEM WITH THE USE OF THE SAME

(75) Inventors: Manabu Kamimura, Tsukuba (JP); Makoto Kiuchi, Tsukuba (JP); Hitoshi Saito, Tsukuba (JP); Maroko Myohara, Ushiku (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 409 days.

(21) Appl. No.: 10/468,422

(22) PCT Filed: Feb. 23, 2001

(86) PCT No.: PCT/JP01/01348

§ 371 (c)(1),
(2), (4) Date: Aug. 18, 2003

(87) PCT Pub. No.: WO02/068643

PCT Pub. Date: Sep. 6, 2002

(65) Prior Publication Data

US 2005/0221458 A1    Oct. 6, 2005

(51) Int. Cl.
*C12N 9/02*    (2006.01)
*C12N 9/58*    (2006.01)
*C12N 15/00*    (2006.01)
*C12P 21/06*    (2006.01)
*A61K 38/00*    (2006.01)
*A01K 67/00*    (2006.01)

(52) U.S. Cl. .................... 435/189; 435/69.1; 435/223; 435/267; 435/272; 435/245; 435/375; 530/300; 536/23.2; 119/270

(58) Field of Classification Search ............... 435/69.1, 435/183, 235.1, 320.1, 348, 223, 189; 530/412, 530/300; 536/23.1; 800/13, 21
See application file for complete search history.

(56) References Cited

FOREIGN PATENT DOCUMENTS

JP    11-123079    5/1999

OTHER PUBLICATIONS

Heisei 10 nendo Kagaku Gijutsu Shinko Choseihi ni yoru Juuten Kiso Kenkyu Seikashuu, Kagaku GijutsuchoKagaku Gijutsu Shinkokyoku, pp. 222-223 (Mar. 1999); with an abridged English translation.
Sonobe H., et al., "Comparative Studies of Ecdysteroid Metabolism between Diapause Eggs and Non-diapause Eggs of the Silkworm, *Bombyx mori.*", *Zoological Science* (Tokyo), vol. 16, No. 6, pp. 935-943 (Dec. 1999).
Christopherson, K.S. et al., "Ecdysteroid-dependent regulation of genes in mammalian cells by a *Drosophila ecdysone* receptor and chimeric transactivators", *Proc. Natl. Acad. Sci. USA*, 89, 6314-6318 (1992).
No, D et al., "Ecdysone-inducible gene expression in mammalian cells and transgenic mice", *Proc. Natl. Acad. Sci. USA*, 93, 3346-3351 (1996).
Martinez, A. et al., "Ecdysone agonist inducible transcription in transgenic tobacco plants", *The Plant Journal*, 19(1), 97-106 (1999).
Kumar et al., "Mycopathologia", vol. 138, No. 3, pp. 141-144 (1997).
Kiuchi et al., "Archives of Insect Biochemistry and Physiology", vol. 52, No. 1, pp. 35-44 (2003).

*Primary Examiner*—Rebecca E. Pruuty
*Assistant Examiner*—Ganapathirama Raghu
(74) *Attorney, Agent, or Firm*—Peter F. Corless; Mark D. Russett; Edwards Angell Palmer & Dodge LLP

(57) ABSTRACT

A material and a system are provided that efficiently inactivate a molting hormone by means of a protein having ecdysteroid 22-oxidase activity.

7 Claims, 9 Drawing Sheets

STRUCTURE AND DETECTION OF ECDYSTEROIDS

EXPRESSION OF ECDYSTEROID 22-OXIDASE USING BACULOVIRUS EXPRESSION SYSTEM

DETECTION BY WESTERN BLOT ANALYSIS OF
ECDYSTEROID 22-OXIDASE (E22O) EXPRESSED
USING BACULOVIRUS EXPRESSION SYSTEM

NON-TREATED
(FIFTH INSTAR
LARVAE PUPATED.)

E220-TREATED
(FOURTH INSTAR
LARVAE FORMED
COCOONS.
BOTH LARVAE AND
COCOONS WERE
SMALLER THAN
CONTROLS.)

E220-TREATED
(FIFTH INSTAR
LARVAE CONTINUED
TO SPIN THREAD,
REMAINED IN A
LARVAL STATE
FOR AT LEAST
10 DAYS,
AND DIED
WITHOUT PUPATING)

NON-TREATED
(FIFTH INSTAR
LARVAE PUPATED
AND THEN HATCHED.)

TRANSCRIPTION INDUCTION OF MOLTING HORMONE RECEPTOR (EcR) B1 ISOFORM mRNA BY 20-HYDROXYECDYSONE (20E) AND 22-DEHYDRO-20-HYDROXYECDYSONE (M20E)

SEQUENCE LISTING

```
<160> NUMBER OF SEQ ID NOS: 8

<210> SEQ ID NO 1
<211> LENGTH: 1963
<212> TYPE: DNA
<213> ORGANISM: Nomuraea rileyi

<400> SEQUENCE: 1
atgacctcct cactcggtct cggtcatcta tcaagcctac tgcttcacag ctcccaagtt      60
tgcgaagcta cttatactac gtggcaacta gaatcgtctt atcgcccacc atgcgaagca     120
aacacatcgt ttgggcgtta tcgcttctcc ctagcacctg ggcattggct ctaccacagg     180
gcggctgtcg atgtataccc ggagaggcgt gctggccatc tgacgagact tgggatgcat     240
tcaactctac cgttgatggc aaactcatca aatccgtccc cctcgcaaag ccgtgttaca     300
cgtcaactga agggtcaggg gatcaatgcc aaaacgtcaa caatgcatgg tcgactgagc     360
gcttccaaac ggcccaggcc ctcggccgat tctatccttt caacacgacc tgcccccgg      420 ttgccaatgg acagcagcca gggacgtgca gtctgggaca gctcccagtc tatgttgtga     480
gagccactga gcattcagac gttgagaaga cgcttgggtt cgttcaagat cacaatatac     540
gtctgtctat caccaacacg ggacatgatc tgaacggccg cggcgacggg ttcggaagtc     600
tgggactctg ggttcaaaac ctccggaaag gtctttctt ccacgaaagc tttaaatctg      660
ccacccagtg cacagaatcg ggctggaatg gcaagtcgat ccacatcgat ggcgcatatc     720 aatgggcga tgtttacgga ttcgccgaga agcataacgt tatcgttgta ggcggtggct      780
cttcaagcgt cggagccact ggaggctggt tatcaggagg cggccacgga ccggcgtcac     840 gaaactacg actcggtgct gatcaactgc tcgaggccga ggtcatgctt gccaacggca      900
ctgtcgtcgt tgccaatcac tgccagcacg ccgatctctt ccgggccctg cgaggcggag     960
gccccggata cggagttgtc ctcggtgtca aagtcaaggc atatcccaac gtcgacaagg    1020
tgactgctca ccatctcacc atcgcccctt cgccaagtcg cctcaacacc agcgccctcg    1080
tcgatgccgt gtccatcatg atgcagtcct tcccggctct caacgagagg ggatacgcag    1140
gatacgccac ctggttccgt tacttgcctg gccctacat cgccaacagt acatctgcct    1200
acacccatag tttctggacc atcggcatga accaggcgga cgcgagtgct gtattcgaac    1260
ctctgcgaag gaagttagcc gaccccggtc tgaatgtggt catcaacagt gacttccagg    1320
```

-continued

```
agtacaacga ctactggtca ttcttccaca acgagctgga caaggccgat atcccgggcg    1380
acactttgct cctcacctcc cgcatgctgg acaagaaggc tttgcatgat ttcgaccgcg    1440
tccgccacat ggtcgaggtt gtgagcggca gacctcaaga gtacaccatg aacttggcta    1500
tgcttgtgtc gggcggcaag gtcttcgccg atgccgccga cacctcttct ggcctcaacc    1560
ctgcctggcg aacctctcct gtggtcctcc tcaccggacg gaagatcccc aagactcaga    1620
ccctgtctct gcaagagcgt caggccattg ccgaggatat gacctcgcac aaagggcagg    1680
cgaccaagga actggccccc gatacggccg gctacatgag cgagggtgat ggcaacgatc    1740
ccgattatat caattctttc tacggccgca attatgcagc tcaccttgca gccaaggaca    1800
agtacgatcc taaacacgtg ttctactgtc ggacgtgtgt tggtgccgag cgattcatca    1860
gtcggcccga gggggcacta tgcagggctt tttagaaaga cggcccatct agatagtgta    1920
gtataagaaa gtagacgttc aattcgaaaa aaaaaaaaa aaa                       1963
```

<210> SEQ ID NO 2
<211> LENGTH: 594
<212> TYPE: PRT
<213> ORGANISM: Nomuraea rileyi

<400> SEQUENCE: 2

```
Met Arg Ser Lys His Ile Val Trp Ala Leu Ser Leu Leu Pro Ser Thr
 1               5                  10                  15

Trp Ala Leu Ala Leu Pro Gln Gly Gly Cys Arg Cys Ile Pro Gly Glu
            20                  25                  30

Ala Cys Trp Pro Ser Asp Glu Thr Trp Asp Ala Phe Asn Ser Thr Val
        35                  40                  45

Asp Gly Lys Leu Ile Lys Ser Val Pro Leu Ala Lys Pro Cys Tyr Thr
    50                  55                  60

Ser Thr Glu Gly Ser Gly Asp Gln Cys Gln Asn Val Asn Asn Ala Trp
65                  70                  75                  80

Ser Thr Glu Arg Phe Gln Thr Ala Gln Ala Leu Gly Arg Phe Tyr Pro
                85                  90                  95

Phe Asn Thr Thr Cys Pro Pro Val Ala Asn Gly Gln Gln Pro Gly Thr
            100                 105                 110

Cys Ser Leu Gly Gln Leu Pro Val Tyr Val Val Arg Ala Thr Glu His
        115                 120                 125

Ser Asp Val Glu Lys Thr Leu Gly Phe Val Gln Asp His Asn Ile Arg
    130                 135                 140

Leu Ser Ile Thr Asn Thr Gly His Asp Leu Asn Gly Arg Gly Asp Gly
145                 150                 155                 160

Phe Gly Ser Leu Gly Leu Trp Val Gln Asn Leu Arg Lys Gly Leu Phe
                165                 170                 175

Phe His Glu Ser Phe Lys Ser Ala Thr Gln Cys Thr Glu Ser Gly Trp
            180                 185                 190

Asn Gly Lys Ser Ile His Ile Asp Gly Ala Tyr Gln Trp Gly Asp Val
        195                 200                 205

Tyr Gly Phe Ala Glu Lys His Asn Val Ile Val Gly Gly Gly Ser
    210                 215                 220

Ser Ser Val Gly Ala Thr Gly Gly Trp Leu Ser Gly Gly His Gly
225                 230                 235                 240

Pro Ala Ser Arg Asn Tyr Gly Leu Gly Ala Asp Gln Leu Leu Glu Ala
                245                 250                 255
```

```
Glu Val Met Leu Ala Asn Gly Thr Val Val Ala Asn His Cys Gln
        260                 265                 270
His Ala Asp Leu Phe Arg Ala Leu Arg Gly Gly Pro Gly Tyr Gly
        275                 280                 285
Val Val Leu Gly Val Lys Val Lys Ala Tyr Pro Asn Val Asp Lys Val
        290                 295                 300
Thr Ala His His Leu Thr Ile Ala Pro Ser Pro Ser Arg Leu Asn Thr
305                     310                 315                 320
Ser Ala Leu Val Asp Ala Val Ser Ile Met Met Gln Ser Phe Pro Ala
                    325                 330                 335
Leu Asn Glu Arg Gly Tyr Ala Gly Tyr Ala Thr Trp Phe Arg Tyr Leu
                340                 345                 350
Pro Gly Pro Tyr Ile Ala Asn Ser Thr Ser Ala Tyr Thr His Ser Phe
                355                 360                 365
Trp Thr Ile Gly Met Asn Gln Ala Asp Ala Ser Ala Val Phe Glu Pro
                370                 375                 380
Leu Arg Arg Lys Leu Ala Asp Pro Gly Leu Asn Val Val Ile Asn Ser
385                 390                 395                 400
Asp Phe Gln Glu Tyr Asn Asp Tyr Trp Ser Phe Phe His Asn Glu Leu
                    405                 410                 415
Asp Lys Ala Asp Ile Pro Gly Asp Thr Leu Leu Leu Thr Ser Arg Met
                420                 425                 430
Leu Asp Lys Lys Ala Leu His Asp Phe Asp Arg Val Arg His Met Val
                435                 440                 445
Glu Val Val Ser Gly Arg Pro Gln Glu Tyr Thr Met Asn Leu Ala Met
                450                 455                 460
Leu Val Ser Gly Gly Lys Val Phe Ala Asp Ala Asp Thr Ser Ser
465                 470                 475                 480
Gly Leu Asn Pro Ala Trp Arg Thr Ser Pro Val Val Leu Leu Thr Gly
                    485                 490                 495
Arg Lys Ile Pro Lys Thr Gln Thr Leu Ser Leu Gln Glu Arg Gln Ala
                500                 505                 510
Ile Ala Glu Asp Met Thr Ser His Lys Gly Gln Ala Thr Lys Glu Leu
                515                 520                 525
Ala Pro Asp Thr Ala Gly Tyr Met Ser Glu Gly Asp Gly Asn Asp Pro
                530                 535                 540
Asp Tyr Ile Asn Ser Phe Tyr Gly Arg Asn Tyr Ala Ala His Leu Ala
545                 550                 555                 560
Ala Lys Asp Lys Tyr Asp Pro Lys His Val Phe Tyr Cys Arg Thr Cys
                565                 570                 575
Val Gly Ala Glu Arg Phe Ile Ser Arg Pro Glu Gly Ala Leu Cys Arg
                580                 585                 590
Ala Phe

<210> SEQ ID NO 3
<211> LENGTH: 15
<212> TYPE: DNA
<213> ORGANISM: Artificial Sequence
```

-continued

```
<220> FEATURE:
<223> OTHER INFORMATION: Description of Artificial Sequence: Synthetic
      Int.R1 primer for RT-PCR

<400> SEQUENCE: 3
tcccargggg tgyag                                                    15

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      Int.R1 primer for RT-PCR

<400> SEQUENCE: 4
tgyagrtgya tccggga                                                  17

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      Int.R1 primer for RT-PCR

<400> SEQUENCE: 5
cagcttttac rttytg                                                   16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      Int.R1 primer for RT-PCR

<400> SEQUENCE: 6
ttactttgcc ytgrtc                                                   16

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      Int.R1 primer for RT-PCR

<400> SEQUENCE: 7
gtgctggcca tctgacgaga ctt                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      Int.R1 primer for RT-PCR

<400> SEQUENCE: 8
ctttgcgagg gggacggatt tga                                           23
```

NOMURAEAE RILEYI-ORIGIN ECDYSTEROID 22-OXIDASE AND MOLT HORMONE INACTIVATION SYSTEM WITH THE USE OF THE SAME

TECHNICAL FIELD

The present invention relates to an ecdysteroid 22-oxidase that is isolated from *Nomuraea rileyi*, which is an entomopathogenic fungus, and a molting hormone inactivation system using same.

BACKGROUND ART

It is known that molting of arthropods, including insects and crustaceans, is induced by several types of ecdysteroids having molting hormone activity.

At least two uses have been developed for these molting hormones.

One of these is the application thereof to growth control, including acceleration of the timing of molting or metamorphosis of individuals and equalization of pupation. This enables, for example, silk thread production in silkworms to be controlled.

The other use is the application thereof to a gene expression system in a cultured cell line, a transgenic animal, or a transgenic plant, the system enabling a high level of expression of a target gene and control of expression timing to be obtained by a molting hormone treatment. This is based on the finding that the molting hormone binds to a molting hormone receptor, which is a transcription factor, and further binds to a molting hormone responsive element on a molting hormone responsive gene, thus controlling the transcription activity of the responsive gene.

For example, a molting hormone receptor and a target gene having a molting hormone responsive element incorporated into its transcription control region are first introduced into these systems, and the intracellular molting hormone concentration is increased by using a method such as addition to a cultured cell line (Christopherson, K. S. et al. (1992) Proc. Natl. Acad. Sci. USA 89, 6314–6318), injection into an animal (No, D et al. (1996) Proc. Natl. Acad. Sci. USA 93, 3346–3351), or absorption via a plant root (Martinez, A. et al. (1999) The Plant Journal 19, 97–106), thus inducing expression of a target gene product. Among these methods, one employing a cultured cell line has already been put into practice as a kit.

On the other hand, a technique for enhancing the activity of the molting hormone without using the molting hormone itself has also been developed. For example, examples thereof include the application to insect pest control of an ecdysteroid having a high molting hormone activity, and a more stable and strong molting hormone agonist having no ecdysteroid skeleton.

In this way, techniques for increasing molting hormone activity have already been developed.

In contrast, hardly any techniques for decreasing molting hormone activity, that is, techniques for inactivating the molting hormone present within a body or cells, have been developed.

A baculovirus-derived ecdysteroid UDP-glucosyltransferase gene (JP, A, 11-123079) has recently been receiving attention as a gene of an enzyme having an ability to inactivate the molting hormone. However, since there are defects such as it being necessary for UDP-glucose to be present at the same time in order for the enzyme to function, it has not yet been put into practice as a purified enzyme preparation or a recombinant protein.

DISCLOSURE OF INVENTION

An object of the present invention is to provide a material and a system that can inactivate the molting hormone efficiently.

In carrying out an intensive investigation in order to achieve this object while recognizing that inactivation of the molting hormone is extremely important in applications such as growth control of insects, etc. and control of induced expression of a target gene product, the present inventors have noted that all ecdysteroids having molting hormone activity have a hydroxyl group at the 22-position, and when this position is modified, the molting hormone activity is markedly degraded. More specifically, it has been found that the above-mentioned object can be attained by isolating an ecdysteroid 22-oxidase from *Nomuraea rileyi*, which is an entomopathogenic fungus, and oxidizing the 22-hydroxyl group of an ecdysteroid into a keto group with this enzyme or a modified protein thereof, and the present invention has thus been accomplished.

That is, the present invention relates to protein (a) or (b) below:

(a) a protein having the amino acid sequence shown by Sequence Listing SEQ ID NO:2, or (b) a protein having an amino acid sequence in which one or a plurality of amino acids are deleted, substituted, or added in Sequence Listing SEQ ID NO:2, the protein having ecdysteroid 22-oxidase activity.

Furthermore, the present invention relates to a gene having DNA (a) or (b) below:

(a) a DNA having the base sequence shown by Sequence Listing SEQ ID NO:1, or (b) a DNA that codes for a protein having ecdysteroid 22-oxidase activity and that hybridizes under stringent conditions with the DNA having the base sequence (a).

Moreover, the present invention relates to a method for inactivating the molting hormone of an arthropod by administering the protein to the arthropod.

Furthermore, the present invention relates to a method for controlling growth of an arthropod by inactivating the molting hormone using the protein.

Moreover, the present invention relates to a method for controlling growth of an insect by inactivating the molting hormone using the protein.

Furthermore, the present invention relates to a method for producing silk thread, the method comprising administering the protein to a silkworm so as to control the diameter of thread spun by the silkworm.

Moreover, the present invention relates to a method for suppressing expression of a molting hormone-inducible gene, the method comprising administering the protein to a transformant.

The protein according to the present invention is an enzyme having activity in oxidizing the 22-hydroxyl group of the molting hormone and inactivating it. Administering this enzyme internally to an arthropod therefore inactivates its molting hormone and enables its growth to be controlled.

The enzyme according to the present invention can be used for controlling the growth of insects including silkworms. In particular, by administering the enzyme according to the present invention to the silkworm, silk thread having high product value due to it being finer than normal silk thread can be produced.

The enzyme according to the present invention can be used for controlling not only the growth of insects but also the growth of crustaceans that use an ecdysteroid as the molting hormone in the same manner as insects.

Furthermore, in order to obtain the enzyme, a system can be employed in which a silkworm is infected with a recombinant baculovirus into which has been incorporated a gene according to the present invention having the base sequence shown by Sequence Listing 2, and a large amount of the protein is expressed in its blood and is collected.

Use of the enzyme or the gene according to the present invention, in a system that induces expression of a target gene product by increasing the intracellular molting hormone concentration by the addition, injection, or root absorption of the molting hormone, enables expression of the target gene to be stopped at will. Therefore, in transformants such as cultured cells, transgenic animals, and transgenic plants, the gene expression system using the molting hormone can be controlled in a negative direction, and this enables the applications of gene expression systems using transformants to be extended.

The present invention is explained in detail below.

BEST MODE FOR CARRYING OUT THE INVENTION

Sequence Listing 1 shows the cDNA of ecdysteroid 22-oxidase isolated from *Nomuraea rileyi* according to the present invention and an amino acid sequence predicted therefrom. Furthermore, Sequence Listing 2 shows a predicted amino acid sequence of the ecdysteroid 22-oxidase.

With regard to cloning of cDNA, a protein is purified from a *Nomuraea rileyi* culture solution using as an indicator the activity for ketonization (oxidation) of the 22-hydroxyl group of ecdysone, which is one type of the molting hormone, and N-terminal and internal amino acid sequences are determined. Moreover, the entire length of the cDNA is cloned by PCR based on these amino acid sequences.

FIG. 1A shows the structures of ecdysteroids found in insect bodies and the products of their oxidation by the enzyme according to the present invention. As shown in FIG. 1B, these ecdysteroids can be easily detected by HPLC. That is, a reverse phase column (TSKgel ODS-80Ts, 4.6 mm×150 mm TOSO) was mounted in an HPLC (LC 10-AT, Shimadzu), and the absorbance at 245 nM was measured by a standard UV detector. In this procedure, the flow rate was 0.6 ml/min, the column retention temperature was 40° C., and a sample was passed in an acetonitrile gradient (20–30%) for 40 minutes.

When a predicted coding region ($A_{111}$-$T_{1893}$ in Sequence Listing 1) of cDNA according to the present invention was expressed in SF-9 cells using a protein expression system (BAC-TO-BAC Baculovirus Expression Systems, Gibco BRL) employing a baculovirus, strong ecdysteroid oxidation activity was observed in the culture solution on the 7th day after starting culturing (FIG. 2). In a Western blot analysis using a polyclonal antibody to the purified present enzyme, it was also confirmed that ecdysteroid 22-oxidase was secreted in the culture solution (FIG. 3).

It is known to a person skilled in the art that, in general, with regard to an amino acid sequence coding for a protein having bioactivity, even when one or a plurality of amino acids are added, deleted, or substituted, the bioactivity can be maintained in some cases. The present invention includes a DNA fragment coding for a protein modified in this manner and having an ecdysteroid 22-oxidase activity. That is, the scope of the present invention also includes a DNA coding for a protein comprising an amino acid sequence of Sequence Listing SEQ ID NO:2 in which one or a plurality of amino acids are added, deleted, substituted, or inserted, the protein having ecdysteroid 22-oxidase activity.

The ‘one or a plurality of’ referred to here usually means 2 to 20, and preferably on the order of 2 to 15, although it depends on the location of the amino acid residue in the tertiary structure of the ecdysteroid 22-oxidase protein at which an amino acid is added, deleted, or substituted, or on the type of the amino acid residue.

A DNA modified in this manner can be obtained by modifying the base sequence of the DNA of the present invention so that a specified amino acid can be deleted, substituted, or added by, for example, a site-directed mutation method.

A modified DNA can also be obtained by subjecting the DNA of the present invention or cells having same to mutation and selecting, from the DNA or the cells, a DNA that hybridizes under stringent conditions with a DNA having the base sequence described by, for example, SEQ ID NO:1 in the Sequence Listing.

The ‘stringent conditions’ referred to here means conditions under which a specific hybrid is formed but no non-specific hybrid is formed. Although it is difficult to express these conditions numerically, the conditions are, for example, those under which nucleic acids having a high homology of at least 99.5% can hybridize, but DNAs having a lower homology than this cannot hybridize.

The present invention is explained below by reference to examples, but the present invention is not limited to the examples below.

EXAMPLE 1

Isolation of Ecdysteroid 22-oxidase from *Nomuraea rileyi*

*Nomuraea rileyi* was cultured for 9 days in a liquid culture medium containing an extract from silkworm larvae, the liquid culture (containing the target enzyme) was passed through a 0.45 μm filter, and then stored at 4° C. After collecting a sufficient amount of liquid culture, the enzyme was isolated by an extraction that involved the following 4 steps.
1. Precipitation by 50% ammonium sulfate.
2. Phenyl hydrophobic chromatography (using phenyl-Sepharose)
3. Gel filtration (using Superdex 200 pg)
4. Anionic chromatography (using HiTrap Q)

2 to 3 were carried out using HPLC (Model Bio-HPLC system, Tosoh).

Figure 1A:
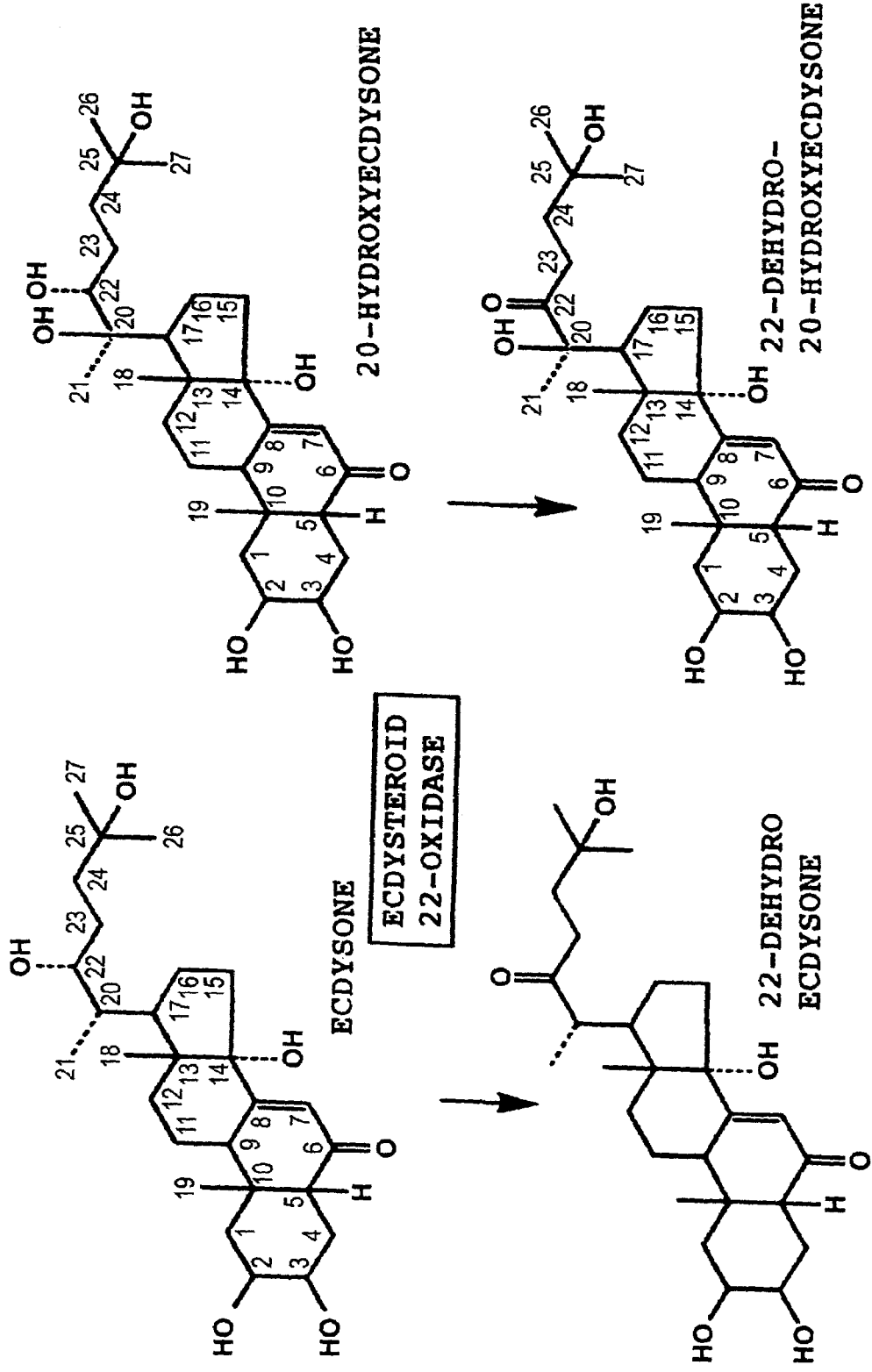
FIG. 1: A shows the structures of ecdysteroids found in insect bodies, and B shows HPLC charts of ecdysteroids and products of oxidation by an enzyme according to the present invention.
Figure 1B:
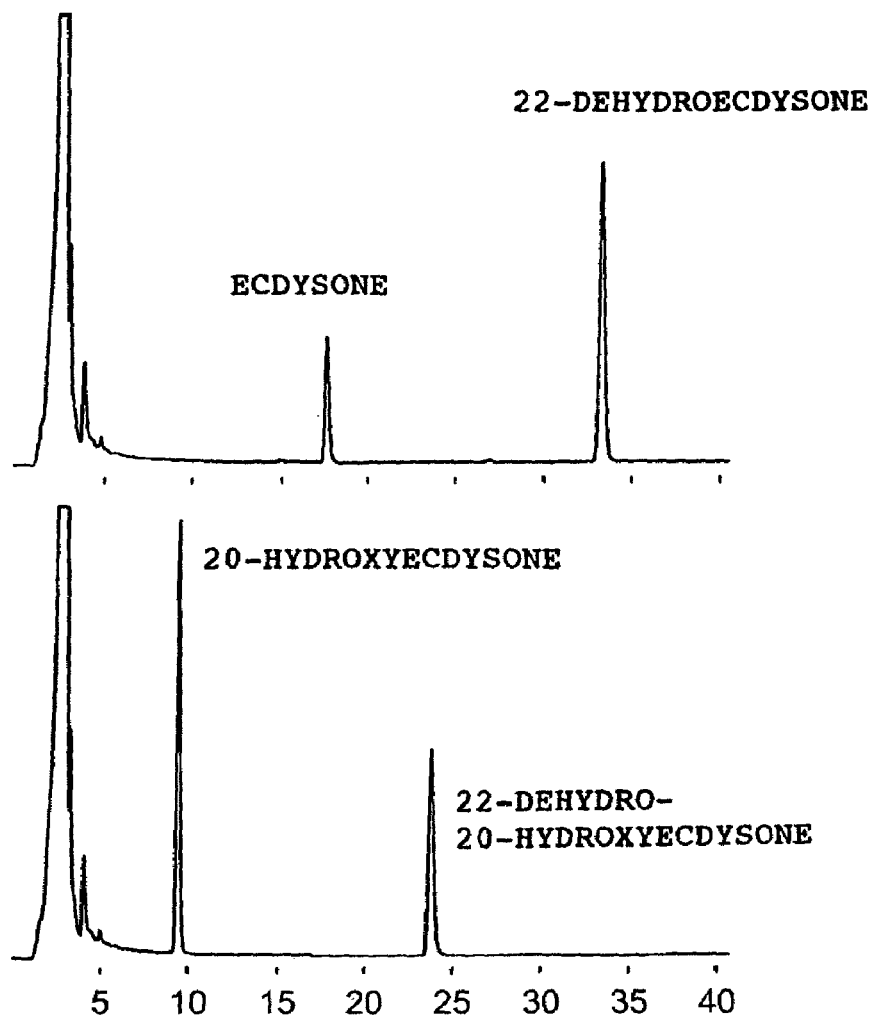
Figure 2:
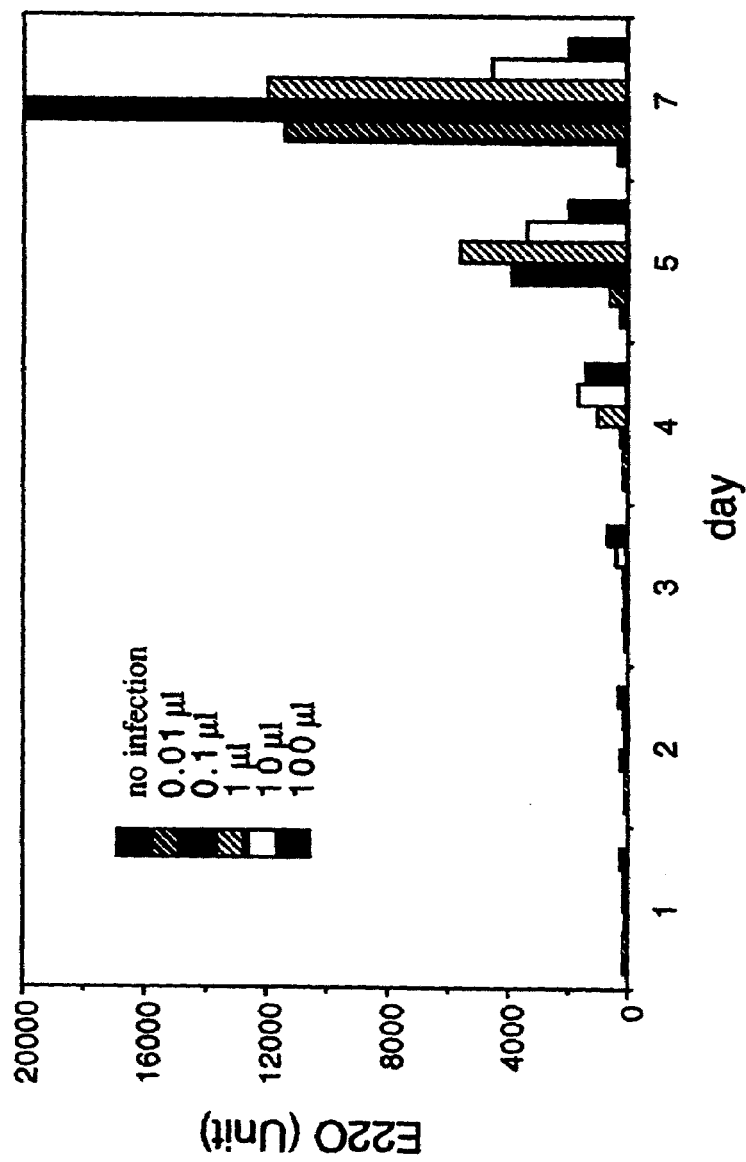
FIG. 2: diagram showing the oxidation activity of the ecdysteroid 22-oxidase expressed by the cDNA according to the present invention.
Figure 3:
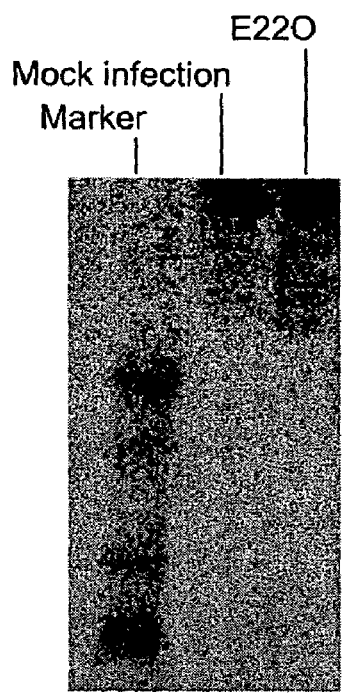
FIG. 3: photographic diagram showing the result of a Western blot analysis using a polyclonal antibody to a purified enzyme according to the present invention.

In each process, an enzyme reaction was carried out using as a substrate ecdysone, which is described in FIG. 1A, and a fraction containing the target enzyme was determined by monitoring an oxidized product using HPLC. After final purification, SDS PAGE was carried out, and it was confirmed by silver staining that a single protein was obtained by the purification.

EXAMPLE 2

Determination of Ecdysteroid 22-oxidase Gene Sequence

The N-terminal sequence of the enzyme isolated according to the method described in Example 1 was first analyzed by an amino acid sequencer to determine the N-terminal amino acid sequence. Furthermore, the N-terminal sequence of a decomposition product obtained by partial decomposition of the enzyme preparation by V8 protease was analyzed by an amino acid sequencer to determine the internal amino acid sequence of this enzyme.

Based on the N-terminal sequence and the internal sequence of the enzyme thus determined, four types of degenerate primers were designed, that is, as forward primers, E22o.6 primer (SEQ ID NO:3; coding for the amino acid sequence LPQGGCR (21 to 27)) and E22o.2 primer (SEQ ID NO:4; coding for the amino acid sequence CRCIPGE (26 to 32)) and, as reverse primers, Int.R1 primer (SEQ ID NO:5; reverse coding for the amino acid sequence QNVNNAW (74 to 80)) and Int.R2 primer (SEQ ID NO:6; reverse coding for the amino acid sequence DQGQNVN (71 to 77)). A partial cDNA of this enzyme was cloned by RT-PCR using these primers and employing mRNA extracted from cultured *Nomuraea rileyi* as a template.

PCR was carried out twice with different primer sets. That is, the E22o.6 primer and the Int.R1 primer were used in the first reaction, and the E22o.2 primer and the Int.R2 primer were used in the second reaction. Finally, the 115 base sequence from 206 to 320 in the molting hormone oxidase cDNA (entire length: 1963 bases) was amplified, and the base sequence was determined.

By designing primers in the partial cDNA thus cloned, and further carrying out 5'RACE and 3'RACE, which are types of modified RT-PCR methods, using the SMART RACE cDNA Amplification Kit (manufactured by CLONTECH), a cDNA covering the entire length of the mRNA of this enzyme was cloned. In the 3'RACE a region from 209 to 1963 of the entire base sequence was amplified using E22o.RF1 primer (SEQ ID NO:7; corresponding to 209 to 231 of the entire base sequence of E22o) and its base sequence was determined. In the 5'RACE, a region from 1 to 290 of the entire base sequence was amplified using E22o.RR1 primer (SEQ ID NO:8; corresponding to the reverse chain of the entire base sequence of E22o) and its base sequence was determined.

By superimposing regions cloned as above by RT-PCR, 5'RACE, and 3'RACE, the entire length of the cDNA of the molting hormone oxidase of *Nomuraea rileyi* was determined.

EXAMPLE 3

Effect of Ecdysteroid 22-oxidase on Silkworm Larvae

Fourth instar and fifth instar silkworm larvae were injected with an enzyme solution containing the enzyme according to the present invention at 1.6 units/20 μl/head, and the growth thereafter was examined. '1 unit' represents the enzyme activity that can oxidize 1 nM of ecdysone in 1 minute.

Figure 4A:
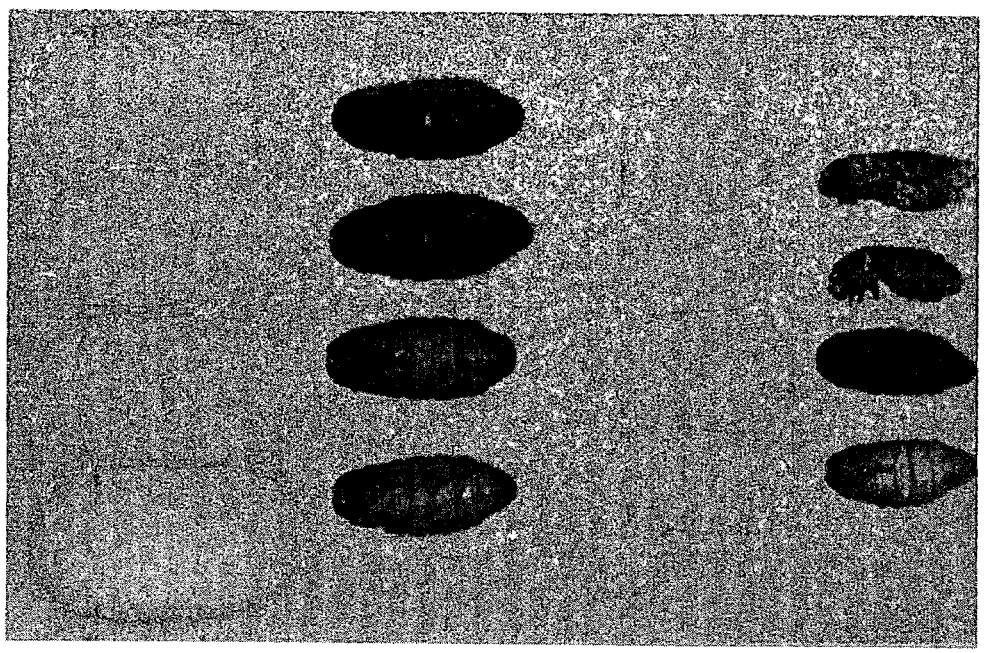
FIG. 4: A and B are photographic diagrams showing the effects of the enzyme according to the present invention respectively on fourth instar larvae (penultimate instar) and fifth instar larvae of silkworms.
Figure 4B:
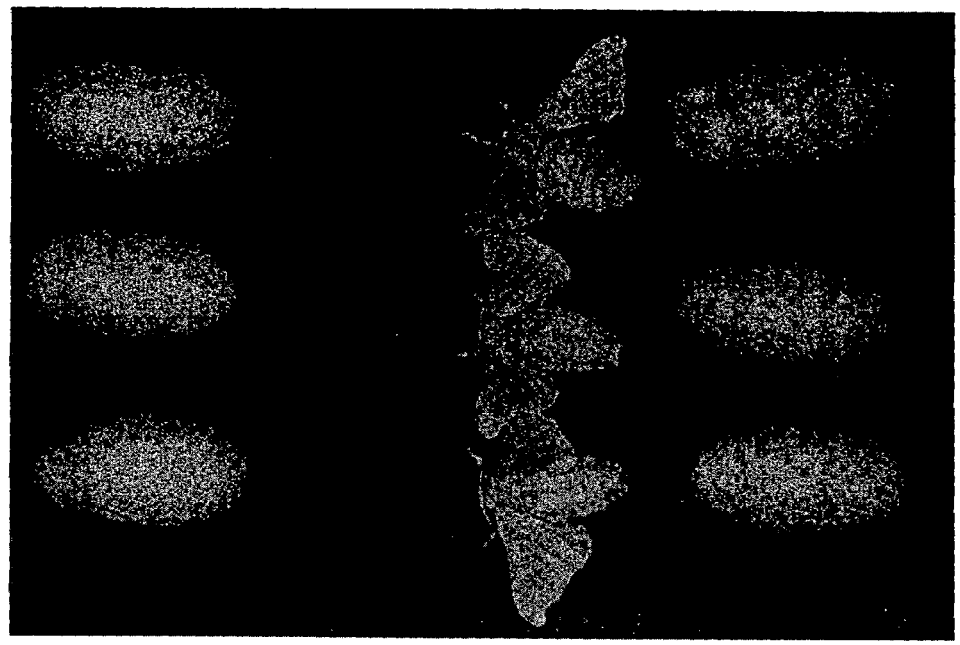
Figure 5A:
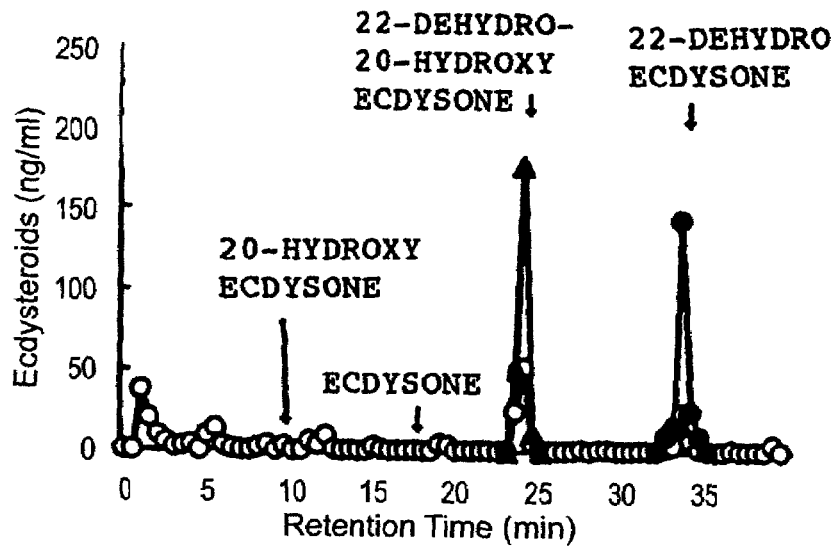
FIG. 5: diagrams showing the accumulation of a modified product in which the 22-hydroxyl group has been oxidized within the bodies of fourth instar larvae (A) and fifth instar larva (B) of silkworms injected with an enzyme solution and a comparison with non-treated fourth instar larvae (C) and non-treated fifth instar larvae (D).
Figure 5B:
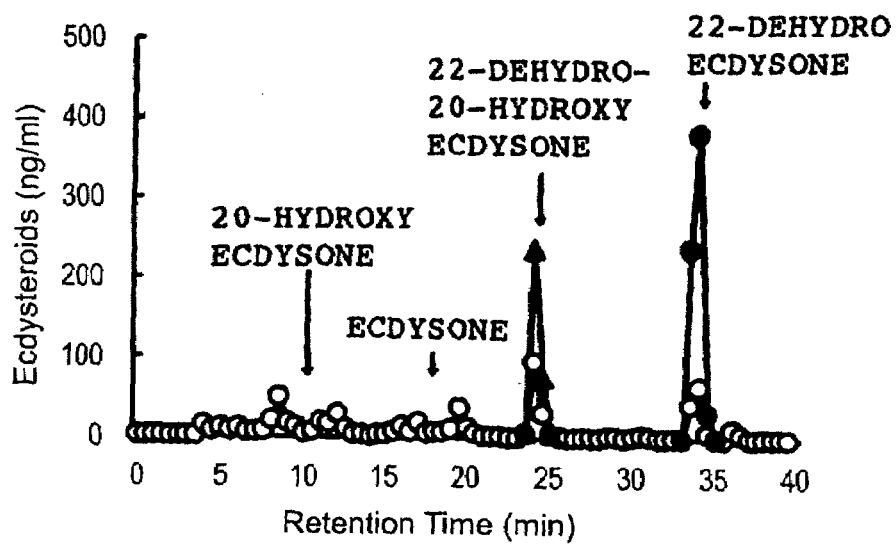
Figure 5C:
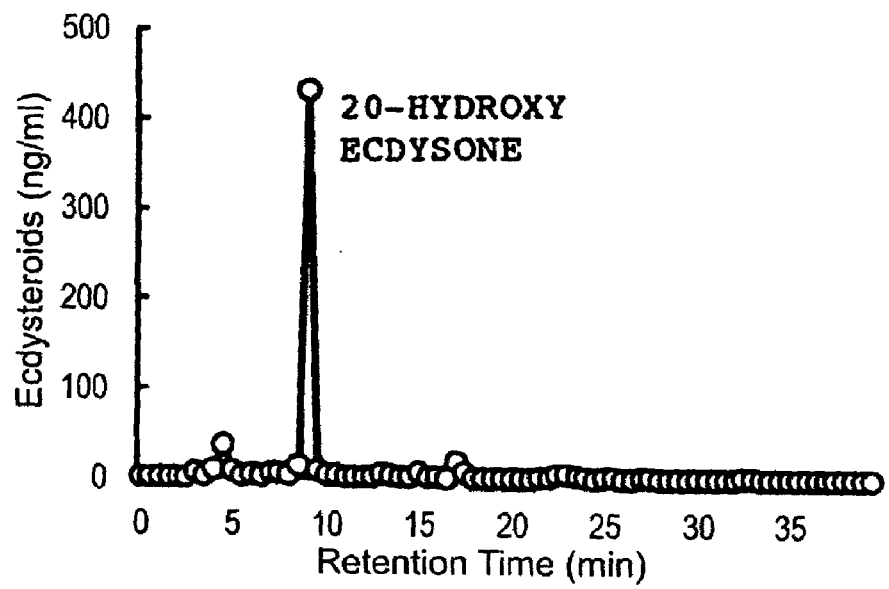
Figure 5D:
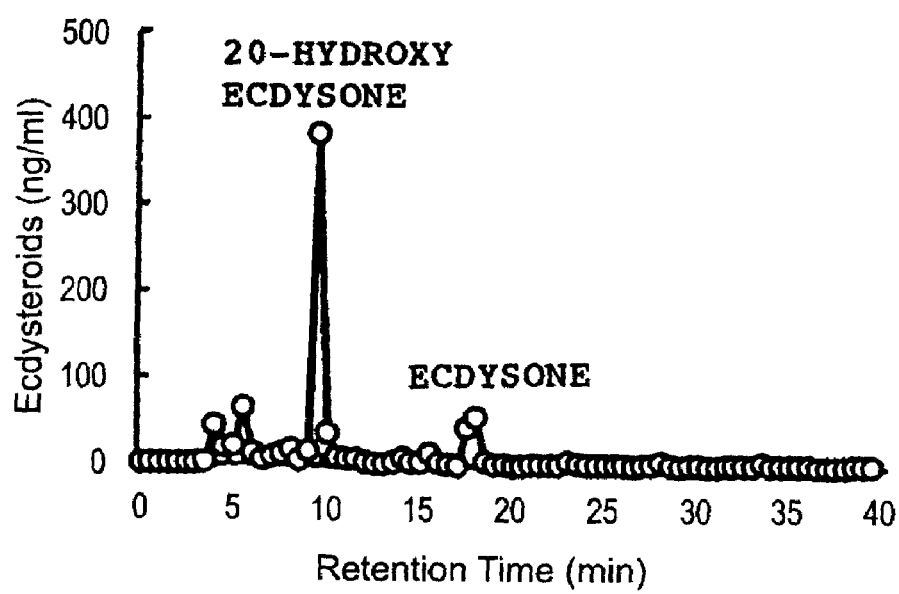

Fourth instar (penultimate instar) silkworm larvae usually molt into fifth instar (final instar) larvae approximately on Day 5, and fifth instar larvae start to form a cocoon approximately on Day 7 and pupate on the 11th day. However, when the present enzyme was injected into the body of a silkworm at the beginning of the fourth instar, it started to form a cocoon approximately 7 days after the injection and pupated 11 days later (FIG. 4A). On the other hand, when it was injected on the 7th day of the fifth instar, it remained in the larval stage for at least 10 days after the injection, and finally died without pupating (FIG. 4B).

In each case, when the ecdysteroid in the blood was examined after injecting the enzyme solution, hardly could any 20-hydroxyecdysone, which is an active form of the molting hormone, or its precursor ecdysone be detected, and it was found that a large amount of the modified products having the 22-hydroxyl group oxidized had accumulated (FIG. 5).

In this way, by injecting a silkworm with the enzyme according to the present invention, the molting hormone within the silkworm body is inactivated, and growth control such as precocious metamorphosis, extension of the spinning period, and inhibition of metamorphosis can be controlled according to the timing of the injection.

EXAMPLE 4

Figure 6:
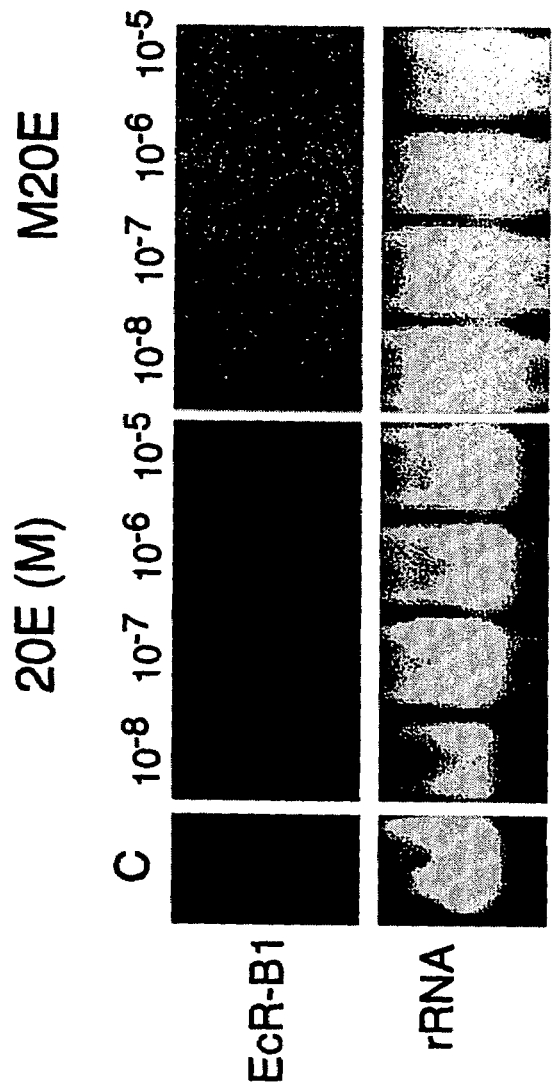
FIG. 6: image analyzer (GS-250, Bio-Rad) showing that 20-hydroxy-22-dehydroecdysone whose 22-position has been modified by the enzyme according to the present invention has no effect in inducing the expression of EcR mRNA.

Transcription Inducing Effect of 22-oxidized Ecdysteroid on Molting Hormone-Inducible Gene It is known that transcription of a molting hormone receptor (EcR) gene is induced by the molting hormone itself, which is a ligand of the gene. Various concentrations of 20-hydroxyecdysone or 20-hydroxy-22-dehydroecdysone whose 22-position had been modified by the enzyme according to the present invention were added to cultured silkworm anterior silk gland, and expression of EcR mRNA was examined after several hours. The result was that, in the case where 20-hydroxyecdysone was added, the expression of EcR mRNA increased in line with the amount added, but in the case where 20-hydroxy-22-dehydroecdysone was added, there was no expression inducing effect (FIG. 6). It was thus confirmed that the ecdysteroid whose 22-position had been modified by the enzyme according to the present invention had no transcription inducing activity for the molting hormone-inducible gene.

As hereinbefore described, the ecdysteroid 22-oxidase according to the present invention has a high ability to inactivate the molting hormone, and use of the enzyme enables growth of an insect and expression of a molting hormone-inducible gene to be controlled effectively.

INDUSTRIAL APPLICABILITY

Use of the enzyme according to the present invention enables growth of an insect to be controlled by efficiently inactivating the insect molting hormone. Furthermore, use of the enzyme enables finer silk thread than usual to be produced. Moreover, use of a gene coding for the enzyme enables expression of the gene to be controlled in a system in which expression of a target gene product is induced by increasing the intracellular molting hormone concentration.

Consequently, the present invention can be applied to the silk thread industry and an industry involved in the production of a specific protein such as, for example, the pharmaceutical industry.

[Sequence Listing Free Text]

[SEQ ID NO:1] Base sequence of DNA coding for *Nomuraea rileyi*-derived ecdysteroid 22-oxidase.

[SEQ ID NO:2] Amino acid sequence of *Nomuraea rileyi*-derived ecdysteroid 22-oxidase.

[SEQ ID NO:3] Description of artificial sequence: E220.6 primer for RT-PCR. 'n' denotes inosine.

[SEQ ID NO:4] Description of artificial sequence: E220.2 primer for RT-PCR. 'n' denotes inosine.

[SEQ ID NO:5] Description of artificial sequence: Int.R1 primer for RT-PCR. 'n' denotes inosine.

[SEQ ID NO:6] Description of artificial sequence: Int.R2 primer for RT-PCR. 'n' denotes inosine.

[SEQ ID NO:7] Description of artificial sequence: EE22o.RF1 primer for modified RT-PCR.

[SEQ ID NO:8] Artificial sequence: EE22o.RR1 primer for modified RT-PCR.

What is claimed is:

1. An isolated protein selected from:
   (a) a protein having the amino acid sequence of SEQ ID NO:2, or
   (b) a modified protein having an amino acid sequence of SEQ ID NO:2 in which one or 2 to 20 amino acids are deleted, substituted, or added, the modified protein having ecdysteroid 22-oxidase activity.

2. An isolated DNA selected from:
(a) a DNA having the nucleotide sequence of SEQ ID NO:1 or
(b) a DNA that encodes a protein having ecdysteroid 22-oxidase activity and hybridizes with the DNA having the nucleotide sequence (a) under conditions under which nucleic acids having a homology of at least 99.5% with the nucleotide sequence (a) can hybridize therewith.

3. A method for producing silk thread, the method comprising administering the protein according to claim 1 to a silkworm so as to control the diameter of silk thread spun by the silkworm; and allowing the silkworm to spin silk thread.

4. A method for suppressing expression of a gene in a non-human transformant, wherein expression of the gene is induced by increasing the intracellular level of an ecdysteroid in the transformant, the method comprising administering the protein according to claim 1 to the transformant, wherein the gene is inducible by 20-hydroxyecdysone and the transformant is an isolated host sell that has been treated with 20-hydroxyecdysone.

5. The isolated protein according to claim 1, which is a protein having the amino acid sequence of SEQ ID NO:2.

6. The isolated DNA according to claim 2, wherein the DNA has the nucleotide sequence of SEQ ID NO:1.

7. The method according to claim 4, wherein the protein is a protein having the amino acid sequence of SEQ ID NO:2.

* * * * *